United States Patent
Bailey et al.

(10) Patent No.: US 11,975,696 B2
(45) Date of Patent: May 7, 2024

(54) METHOD OF REMOVING MALODOR USING GASEOUS CLEANING AGENT

(71) Applicant: NUVINAIR, LLC, Plano, TX (US)

(72) Inventors: Kyle Bailey, Plano, TX (US); Jason Bailey, Plano, TX (US)

(73) Assignee: NUVINAIR, LLC, Plano, TX (US)

( * ) Notice: Subject to any disclaimer, the term of this patent is extended or adjusted under 35 U.S.C. 154(b) by 0 days.

(21) Appl. No.: 17/989,454

(22) Filed: Nov. 17, 2022

(65) Prior Publication Data

US 2023/0085817 A1 Mar. 23, 2023

Related U.S. Application Data

(60) Continuation of application No. 16/835,851, filed on Mar. 31, 2020, now Pat. No. 11,535,205, which is a
(Continued)

(51) Int. Cl.
*A61L 2/00* (2006.01)
*A61L 2/22* (2006.01)
(Continued)

(52) U.S. Cl.
CPC .............. *B60S 3/008* (2013.01); *A61L 2/22* (2013.01); *A61L 9/14* (2013.01); *B08B 3/02* (2013.01);
(Continued)

(58) Field of Classification Search
CPC . B05B 17/11; B60H 3/007; A61L 9/01; A61L 2/00; A61L 2/22; A61L 9/00; B05C 9/00; B01F 3/02
(Continued)

(56) References Cited

U.S. PATENT DOCUMENTS

| 3,420,509 A | 1/1969 | Katzman et al. |
| D262,821 S | 1/1982 | Poore |
| | (Continued) | |

FOREIGN PATENT DOCUMENTS

| CN | 1582661 A | 2/2005 |
| CN | 101495190 A | 7/2009 |
| | (Continued) | |

OTHER PUBLICATIONS

"CLo2 Efficiency System Demo 8 2015" YouTube Aug. 19, 2015 by ACES Environmental Svcs, LLC.
(Continued)

*Primary Examiner* — Monzer R Chorbaji
(74) *Attorney, Agent, or Firm* — Stephen Y. Liu; J. Miguel Hernandez; Carstens, Allen & Gourley, LLP

(57) ABSTRACT

There is provided a system and method of cleaning surfaces of an enclosable environment of a contamination comprising a microbial and viral load. The method includes the steps of sealing the enclosable environment and placing water, and a solid or gel pack, into a container and generating a vortex the container by rotating an impeller. The agitation causes the solid or gel pack to release a gaseous cleaning agent. An air-borne spray exiting from the container spreads throughout the enclosable environment to contact the surfaces to be cleaned within the enclosable environment. The enclosable environment is maintained closed for an effective time period while the air-borne spray dwells on the surfaces to eliminate or substantially reduce the load of the contamination.

24 Claims, 10 Drawing Sheets

Related U.S. Application Data continuation-in-part of application No. 15/895,510, filed on Feb. 13, 2018, now Pat. No. 11,420,599, which is a continuation of application No. 15/253,315, filed on Aug. 31, 2016, now Pat. No. 9,925,959, which is a division of application No. 15/063,931, filed on Mar. 8, 2016, now Pat. No. 9,446,742.

(60) Provisional application No. 62/253,188, filed on Nov. 10, 2015.

(51) Int. Cl.
*A61L 9/14* (2006.01)
*A62B 7/08* (2006.01)
*B08B 3/02* (2006.01)
*B08B 3/04* (2006.01)
*B08B 9/00* (2006.01)
*B60S 3/00* (2006.01)

(52) U.S. Cl.
CPC .............. *B08B 3/04* (2013.01); *B08B 9/00* (2013.01); *A61L 2202/16* (2013.01); *A61L 2202/17* (2013.01)

(58) Field of Classification Search
USPC .............................. 422/1, 5, 28, 32, 37, 122
See application file for complete search history.

(56) References Cited

U.S. PATENT DOCUMENTS

| | | | |
|---|---|---|---|
| 4,482,365 A | 11/1984 | Roach | |
| 5,549,854 A | 8/1996 | Hulthom et al. | |
| 6,273,402 B1 | 8/2001 | Cheng | |
| 6,764,661 B1 | 7/2004 | Girard | |
| D588,687 S | 3/2009 | Drucker et al. | |
| 7,846,227 B2 | 12/2010 | Gotoh et al. | |
| D635,403 S | 4/2011 | Conway et al. | |
| D648,016 S | 11/2011 | Choi et al. | |
| 8,221,678 B2* | 7/2012 | Hedman | A61L 2/16 422/1 |
| D711,523 S | 8/2014 | Hsiao | |
| D711,524 S | 8/2014 | Hsiao | |
| 9,433,695 B2 | 9/2016 | Aamodt et al. | |
| 9,446,742 B1* | 9/2016 | Bailey | B08B 3/02 |
| D795,407 S | 8/2017 | Skoda et al. | |
| 9,925,959 B2* | 3/2018 | Bailey | B08B 3/04 |
| D952,824 S | 5/2022 | Yang | |
| 11,420,599 B2* | 8/2022 | Bailey | A61L 2/22 |
| D997,327 S | 8/2023 | Xing et al. | |
| 2004/0009094 A1 | 1/2004 | Adiga et al. | |
| 2005/0031486 A1* | 2/2005 | Mole | A61L 2/24 422/62 |
| 2005/0074359 A1 | 4/2005 | Krieger et al. | |
| 2006/0067854 A1 | 3/2006 | Andino et al. | |
| 2008/0283626 A1 | 11/2008 | Aldana et al. | |
| 2008/0292507 A1 | 11/2008 | Dee et al. | |
| 2009/0148342 A1 | 6/2009 | Bromberg et al. | |
| 2012/0174792 A1* | 7/2012 | Chang | A61L 9/22 96/52 |
| 2013/0028787 A1 | 1/2013 | Takeuchi et al. | |
| 2013/0079733 A1* | 3/2013 | Burt | B05B 17/0607 239/102.1 |
| 2013/0136685 A1 | 5/2013 | Baselli et al. | |
| 2013/0189153 A1 | 7/2013 | Carson et al. | |
| 2014/0115765 A1 | 5/2014 | Carpenter et al. | |
| 2014/0271355 A1 | 9/2014 | Mason | |
| 2023/0398250 A1 | 12/2023 | Bailey et al. | |

FOREIGN PATENT DOCUMENTS

| | | |
|---|---|---|
| CN | 101537203 A | 9/2009 |
| CN | 104321137 A | 1/2015 |
| JP | 2003040712 A | 2/2003 |
| JP | 2009051018 A | 3/2009 |
| JP | 2009234887 A | 10/2009 |
| KR | 101457648 B1 | 10/2014 |
| WO | 2006076033 A1 | 7/2006 |
| WO | 2009114962 A1 | 9/2009 |
| WO | 2015100866 A1 | 7/2015 |
| WO | 2017091354 A2 | 6/2017 |

OTHER PUBLICATIONS

"How to Use a Biocide Systems Car Deoderizer" YouTube Jun. 16, 2014 by StreetsideAuto.com.

"Odor Removal & Ozone Generator Usage" YouTube Mar. 12, 2009 by Detail King.

Air Clenz Ordor Eliminating Tablet, www.airclenz.com, Feb. 6, 2014, 11 pages.

Biocide Systems, "Auto Shocker Quick Release Care Odor Eliminator", dated Jul. 30, 2013, https://web.archive.org/web/20130730134349/http://www.biocidesystems.com:80/autoshocker1.html, accessed on Dec. 9, 2023, 3 pages.

Promixx The Original Vortex Mixer & Best Protein Shaker, "Introducing the World's Most Advanced Sports Bottle!", dated Oct. 29, 2014, https://web.archive.org/web/20141029052233/http://www.promixx.com/, accessed Dec. 5, 2023, 7 pages.

* cited by examiner

METHOD OF REMOVING MALODOR USING GASEOUS CLEANING AGENT

STATEMENT OF RELATED APPLICATIONS

This application is a continuation of U.S. Ser. No. 16/835,851, filed on Mar. 31, 2020, which is a continuation-in-part application of U.S. Ser. No. 15/895,510 filed Feb. 13, 2018, issued as U.S. Pat. No. 11,420,599 which is in turn a continuation of application U.S. Ser. No 15/253,315 filed Aug. 31, 2016, issued as U.S. Pat. No. 9,925,959, which is in turn a divisional application of U.S. Ser. No. 15/063,931, filed on Mar. 8, 2016, and issued as U.S. Pat. No. 9,446,742, which is in turn a continuation of provisional application 62/253,188 filed on Nov. 10, 2015.

BACKGROUND

1. Field of the Invention

The present technology relates to apparatus and systems for air-borne dispersal of a cleaning agent onto contaminated surfaces to clean these surfaces. More particularly, the technology relates to cleaning of surfaces, contaminated with microbial and/or a viral load that may be hazardous to human health and that may lead to contagion, in enclosed spaces, such as vehicle people-carrying spaces, to reduce or eliminate the contamination.

2. Description of the Related Art

There is increasing concern about the spread of contagious diseases, whether these may be influenza, common colds, corona viruses (SARS, MERS, COVID-19), or a potentially lethal virus such as Ebola, or microbial or viral diseases that are not even known or identified at this time. For purposes of this description, microscopic fungi, bacteria and viruses are included in the term "microbes." Most of these microbes and viruses are spread through contact; a first person contacts some surface (for example, by shaking the hand of a contagious person or touches a contaminated surface) and acquires the contamination, becomes infected, and then passes it on to yet another person. This chain of infection is well-known. Some contaminants, whether microbial or viral, appear to be spread through "air-borne" means. This includes coughing and the emitting of a fine spray of contaminated and contagious sputum.

In a modern urban environment, one of the main means of transportation is in enclosed vehicles such as, but not limited to, aircraft, busses, trains, boats, cars, SUVs and trucks. Some of these are vehicles that are open to the general public to use, and some members of the public may have a communicable disease that is spread through microbes or viruses. Surfaces inside the cabin of the vehicle, where passengers are usually seated, may over time become heavily contaminated with live microbes and viral contaminants. Thus, these surfaces serve to spread the microbial or viral disease to other passengers through contact.

Even in non-public, personal or family transportation, one family member may be ill and could contaminate surfaces thereby passing a contagious illness to other family members. This is especially a risk where school-aged children "pick up" a microbial or viral infection from classmates at school, and can then pass it on to parents and siblings through contaminated surfaces in a family vehicle. Some microbes or viruses may be long-lived, and immunity to these may not be readily achieved. Thus, there is a chance of recurrent illness. Merely wiping surfaces may not eliminate the microbial or viral load on surfaces because surfaces may not be smooth and totally accessible. For example, surfaces are often textured and may have joints and other features where microbial and viral loads may persist.

With regard to newly manufactured vehicles, the chances of a microbial or viral load on surfaces are low, unless the vehicle was contaminated during assembly. On the other hand, the chances that a "pre-owned" or "used" vehicle is contaminated and a source of potential infection, is relatively far higher. Aside from the potential health issues, there are often also aesthetic issues with pre-owned or used cars: they may have an odor in the cabin space from pets carried in the space or from the way in which they were (mis)used by the previous owners. This can have a negative impact on the resale value of the vehicle.

There is a need from a public health standpoint to clean surfaces within a passenger carrying cabin space of vehicles to reduce any microbial and/or viral load. Moreover, there is also not only a public health need to do this but also a business or economic need to remove any undesirable odors from the cabin space of public, used or pre-owned vehicles.

There are other spaces besides where microbial contaminations may linger as well. These include but are not limited to: rooms in a house, hotel rooms, hospital rooms, rooms in homes for the aged, intensive care units, surgery rooms, yoga rooms, gyms, restaurants, ships cabins and passenger-use spaces on cruise vessels, trains, buses, aircraft cabins, etc. In general, living spaces and other spaces that humans use regularly and that contain surfaces on which microbes can dwell, are a potential source for spread of infections.

SUMMARY

This summary is intended to present a brief outline of some of the features of exemplary embodiments of the inventions; these and additional features are more particularly described in the Detailed Description, here below. The descriptions do not limit the scope on the inventions, which is set forth in the appended patent claims.

In an exemplary embodiment, there is provided a method of cleaning contaminated surfaces in an enclosable environment. The contamination may comprise any one or more of a microbial load, a viral load, and malodorous matter. The exemplary method includes placing water and a solid or gel pack into a container of a treatment apparatus in the enclosable environment. The solid or gel pack is configured to release a gaseous cleaning agent upon mixing with water. Then, sealing the enclosable environment with the treatment apparatus contained therein. Automatically, by preset timer, activating a motor of the treatment apparatus to agitate the water with an impeller in the container to thereby generate a vortex of water within the container of the treatment apparatus. The generation of the vortex causes an air-borne spray of liquid and gaseous cleaning agent to exit from a top end of the container and to contact the contaminated surfaces in the enclosable environment and decontaminating the surfaces. Automatically terminating the motor when the preset timer has elapsed.

An example of the apparatus used in carrying out this method includes a container mounted to a housing. The housing contains an electric motor and is releasably and sealingly attached to the container. The apparatus has a base so that the apparatus can stand upright when assembled and in use. The container includes a spindle with an impeller, driven by an electric motor of the apparatus, to agitate the water with the solid or the gel pack in the container. The container has a lid, sized and configured to releasably and sealingly engage an upper end of the container. The lid has a liquid baffle inside, and the lid has a nozzle extending from the lid.

In addition, the exemplary apparatus may have an electronic timer that may have several preset times so that the apparatus can be set to operate, i.e. rotate the impeller and create a vortex, for a selected one of the preset times. The timer may be "in-line" meaning that it may be located in the power line to the apparatus. In an exemplary embodiment of the timer, it has a time-delay to allow a user to set up the apparatus in the enclosable environment to be treated, and vacate the enclosable environment before the power turns on and the motor activates so that gaseous cleaning agent is generated. Further, once the preset time selected has expired, the apparatus turns off the motor driving the impeller. After a period of time after the motor has stopped, a light, such as a low power LED, located to be visible to the operator commences flashing or otherwise indicating to the operator that the treatment procedure is complete and that it is safe to access the space for activities, such as to retrieve the apparatus for use in a next cleaning operation.

Optionally, sealing the enclosable environment having contaminated surfaces therein, comprises closing doors, windows and air vents of an air circulation system. The air vents of the circulation system may also be set in a recirculating mode in order to clean the interior of the air ductwork.

Optionally, the solid or gel pack includes a formulation that upon contact with water releases chlorine dioxide as the gaseous cleaning agent.

Optionally, during cleaning of the enclosable environment having contaminated surfaces therein, an air circulation system may be turned on to assist in dispersing the air-borne mist of liquid and gaseous cleaning agent.

Optionally, the enclosable environment having contaminated surfaces therein remains sealed while the air-borne spray dwells on the surfaces to eliminate, or substantially reduce, the load of the contamination for an effective time period of at least about 3 to about 8 minutes, which may be set using a timer. The timer activates the motor of the apparatus and sets the time duration for motor operation spreading the air-borne spray of the liquid/gaseous cleaning agent. Upon expiration of the preset time, the timer stops the motor. The apparatus may automatically activate a light to indicate when the concentration of gaseous cleaning agent is at a safe level. This automatic light activation may be set to start at a time after the timer preset period has elapsed, to allow the enclosable environment to be safe in terms of residual gaseous cleaning agent concentration. Or, the light might be set manually and independently of the timer, but with reference to the timer, to ensure light activation after elapse of such time after the timer preset operating period has elapsed, as to allow the enclosable environment to be safe to enter in terms of residual gaseous cleaning agent concentration. As an alternative, or in addition to the light, an audible alarm may also be used to alert the operator that the enclosable environment is safe to enter.

Optionally, the motor of the apparatus is powered by a rechargeable battery or by a connection to a power outlet located within the enclosable environment, or outside of it.

Optionally, when the enclosable environment is a vehicular cabin, the apparatus is sized to fit inside a cup-holder of the cabin space.

Optionally, the step of activating the motor of the apparatus is carried out remotely via WIFI or Bluetooth using a timer on an app on a smart phone that is in communication with the apparatus to activate the motor of the apparatus.

Optionally, the coating from the air-borne spray dwells on the interior of the surfaces of the cabin space, room space or enclosable environment having contaminated surfaces therein cabin long enough to eliminate or substantially reduce malodors.

BRIEF DESCRIPTION OF THE DRAWINGS

The foregoing aspects and many of the attendant advantages, of the present technology will become more readily appreciated by reference to the following Detailed Description, when taken in conjunction with the accompanying simplified drawings of exemplary embodiments. The drawings, briefly described here below, are not to scale, are presented for ease of explanation and do not limit the scope of the inventions recited in the accompanying patent claims.

DETAILED DESCRIPTION

Figure 1:
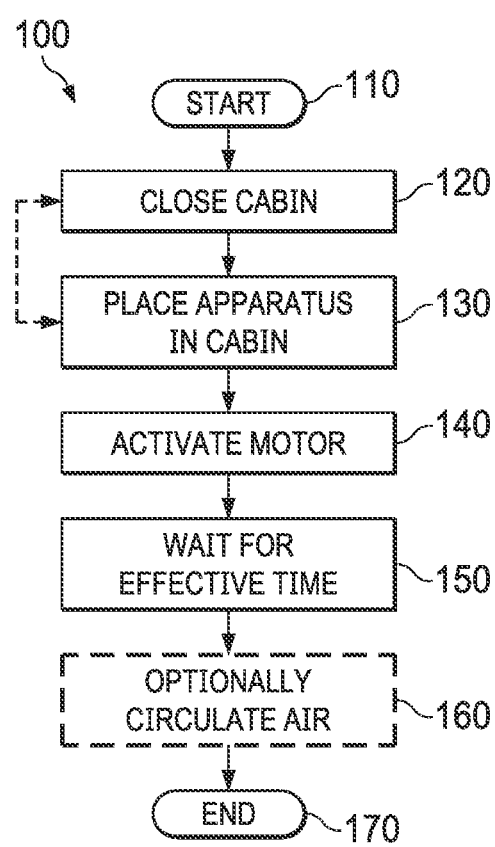
FIG. 1 is a schematic flow diagram of an exemplary embodiment illustrating some of the steps of the method of cleaning contaminated surfaces in an enclosed space.

In The following non-limiting detailed descriptions of examples of embodiments of the inventions may refer to appended Figure drawings and are not limited to the drawings, which are merely presented for enhancing explanations of features of the technology. In addition, the detailed descriptions may refer to particular terms of art, some of which are defined herein, as appropriate and necessary for clarity.

The term "cabin" as used in the specification and claims refer to a space containing contaminated surfaces that can readily be enclosed, for example by closing doors, windows and air vent system, if any, of the space such that air inside the space is neither withdrawn nor added to. The air may be allowed to re-circulate in the cabin however, by activation of an air circulation system, for example, or use of a fan in the cabin. This is useful to also treat ductwork in the air circulation system to remove malodors and to remove or reduce any microbial or viral load.

The terms "enclosable environment," or enclosable space" is meant as synonymous with "cabin," but for the sake of clarity these terms include, but are not limited to, rooms in a house, hotel rooms, hospital rooms, rooms in homes for the aged, intensive care units, surgery rooms, yoga rooms, gyms, restaurants, ships cabins and passenger-use spaces on cruise vessels, trains, buses, aircraft cabins, and the like. So, this should not be read as limited to commonly understood vehicular cabins. In general, the terms encompass living spaces, and other spaces, that humans use regularly, even if intermittently, and that contain surfaces on which microbial life forms can dwell as a potential source for spread of infection.

The term "coating" or "coat" as is used in reference to a coating a cleaning agent onto surfaces, means that the cleaning agent (by an air-borne mist of fine liquid droplets and a gaseous cleaning agent) contacts the surfaces, and the coating may be discontinuous in some contacted areas of surface. The surfaces may include, but are not limited to, fine surface textures, surface patterns, and tight interstitial spaces such as found, for example, in stitched seats and dash boards, couches, textiles, tiles, bedding, carpets, table tops, chairs, floors, wood, interior boundaries (such as walls, ceilings), cabinets, beds, bedding materials, etc.

The terms "contamination" or "contamination load" when used in reference to surfaces within a cabin means microbial, fungal, or viral contamination and also includes contaminants that cause a malodorous scent, for example, of decayed organic matter, fecal matter, and the like.

The term "effective period of time" as it relates to the time that the cleaning agent dwells in a cabin for cleaning of surfaces therein, the effective period may vary from about 3 to about 20 minutes; and in particular may be from about 3 to about 10 minutes. More or less time may also be effective, depending upon the degree of cleaning (extent of contaminant load reduction) to be achieved, the nature of the chemical cleaning agent used, and the number of repetitions of treatment sequentially, if such repetition is necessary. For example, some cabin spaces may have surfaces so heavily contaminated as to require more than one treatment, or to require that the gaseous cleaning agent dwell on surfaces for up to 8 hours, or overnight, to achieve a desired level of cleanliness, deodorization, sanitization or disinfection, as applicable.

The term "sealing" in the context of sealing a cabin or an enclosable environment/space means that windows doors and other ingress or exit points are closed. However, if the cabin or the enclosable environment/space has an air duct system that can be set to recirculate air, then setting it to recirculate falls within the meaning of the term "sealing" and it allows potential cleaning of the air duct system.

The term "significant reduction in contamination load" means that the contamination load of a particular contaminating species is reduced by at least 80% after cleaning in exemplary embodiments, or in some exemplary embodiments at least 98% after cleaning.

Several of the following examples discussed in relation to the Figures may relate, for ease of explanation, to vehicles, but it should be understood that the explanations are also applicable to "enclosable environments," as defined herein.

Figure 2A:
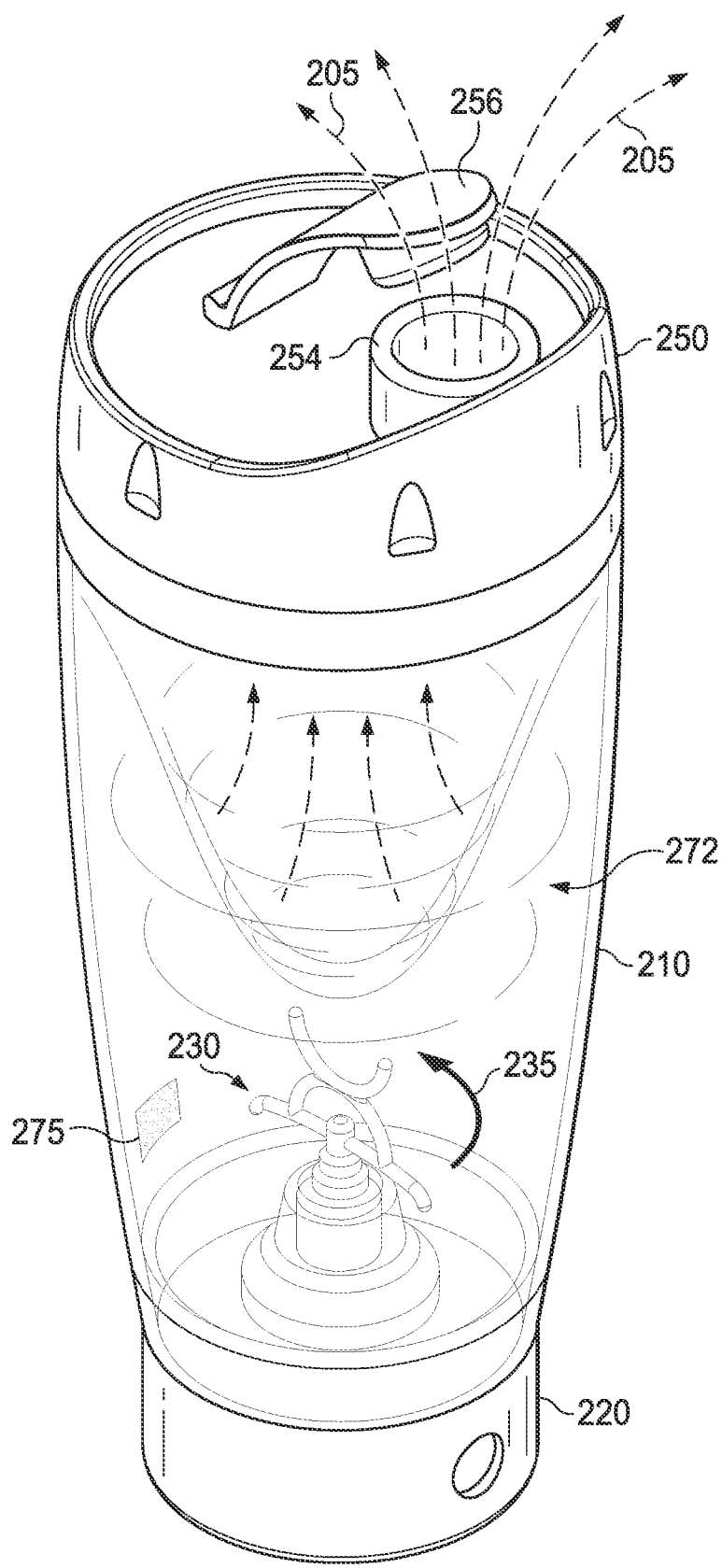
FIG. 2A is an exemplary embodiment of an apparatus showing the generation of a gaseous cleaning agent from its container.
Figure 2B:
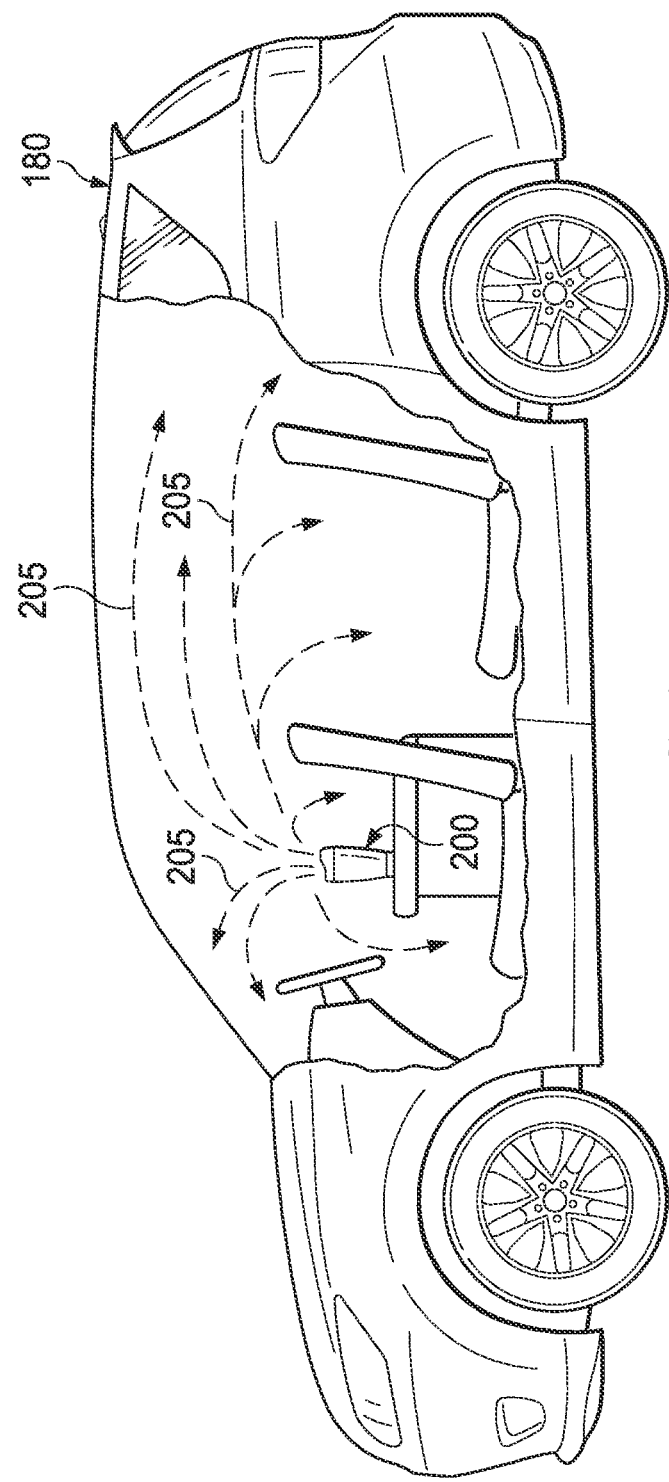
FIG. 2B is an exemplary cutaway illustration of a vehicle showing the exemplary embodiment of the apparatus of FIG. 2A emitting an air-borne gaseous cleaning agent throughout the cabin.

Referring to FIG. 1, an exemplary flowchart, there are several straightforward steps in the system or method depicted. Once the process starts at block 110, the cabin with contaminated surfaces inside to be treated is closed at block 120. For example, in a used car such as exemplified in FIG. 2 as 180, all doors, windows and the air circulation system, are closed off. Thus, air does not enter or leave the cabin except for natural flow around seals of doors and windows, which may occur in a closed cabin. A door is opened, and an apparatus (explained later with reference to FIGS. 3A and B, and 4A and B) containing liquid with a chemical in solid or gel pack form is placed in the cabin at block 130, and the cabin is closed. (Note that step 120 may take place after step 130; the order is not important). After a few minutes, the chemical in the closed apparatus generates a gaseous cleaning agent and the water becomes slightly cloudy as a result. At this stage the motor of the apparatus is activated in block 140. A nozzle of the apparatus is open, if it was not open already, and the nozzle is sized such that flow of gaseous agent through the nozzle erupts upward, as lava from a volcano, and flows throughout the cabin interior, as shown in FIG. 2B by arrows 205. The nozzle, as explained below, has internal structures, like baffles, that remove entrained large liquid droplets from the gaseous cleaning agent stream as it exits from the apparatus. It is theorized, without being bound, that smaller fine droplets are entrained and assist in the coating and permeation of surfaces with the gaseous cleaning agent. As with any chemical cleaning agent, the agent should be allowed to dwell on the surfaces for a period of time effective for a significant reduction in the contamination load, as in block 150. Optionally, during this period of waiting (block 150), the vehicle being treated (block 160) may activate the air circulation system, in recirculation mode. this would allow the cleaning agent to enter the ducting and filters that form part of the air circulation system and clean these of potential allergens, microbes, viruses and fungi, as well. After an effective period of time has elapsed, and entry into the cabin is deemed safe, the cabin can be opened in block 170, and the cleaning process is complete.

An exemplary embodiment of an apparatus useful in carrying out the systems and methods of the invention is illustrated in FIGS. 3A, 3B and 4A and 4B. As shown, the apparatus 200 has a container 210, with sides that are gently convex-curved, and that has a base 220 at one end and a lid 250 at the other end. The container 210 has a diameter 212 at its upper end that is larger than its diameter 214 near its base 220. The base 220 contains a motor driven by either a battery pack (rechargeable or not) inside the base, or by electrical connection to an electrical outlet. A spindle 226 is seated on an engaging wheel 224 that engages with motor spindle 222 and rotates in unison with motor spindle 222. An impeller 230 has a cavity 232 that friction fits to the spindle 226 so that the impeller 230 rotates as the spindle 226 rotates. The impeller in the exemplary embodiment shown has a "double horse-shoe shape" with one horse shoe 234 curved downward, and the other 236 curved upward so that the two are conjoined in a common plane at their respective apexes of curvature. This design facilitates creation of a vortex shape when liquid in container 210 is agitated by the rotating impeller in the container at speed, although other impeller shapes may also achieve the function of vortex creation. A protective cover 228 shields the motor from contents of the container 210, and fits around the spindle 226, which projects out axially through a hole in the center of the cover. The spindle is appropriately sealed against the hole to avoid or minimize leakage into a space under the cover 228.

Figure 4A:
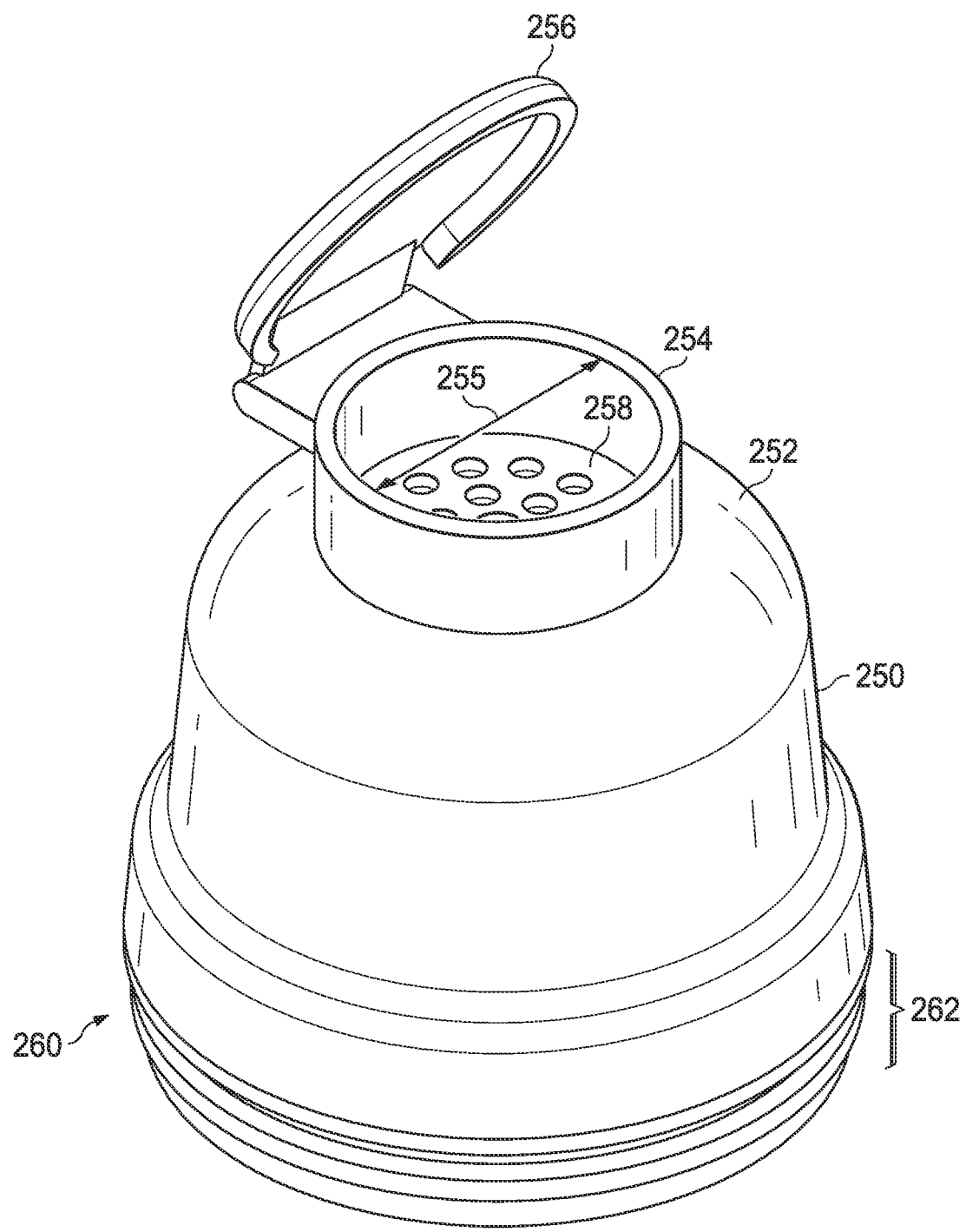
FIGS. 4A and B depict alternative views of another exemplary lid for an exemplary apparatus like that of FIGS. 3A and B.
Figure 4B:
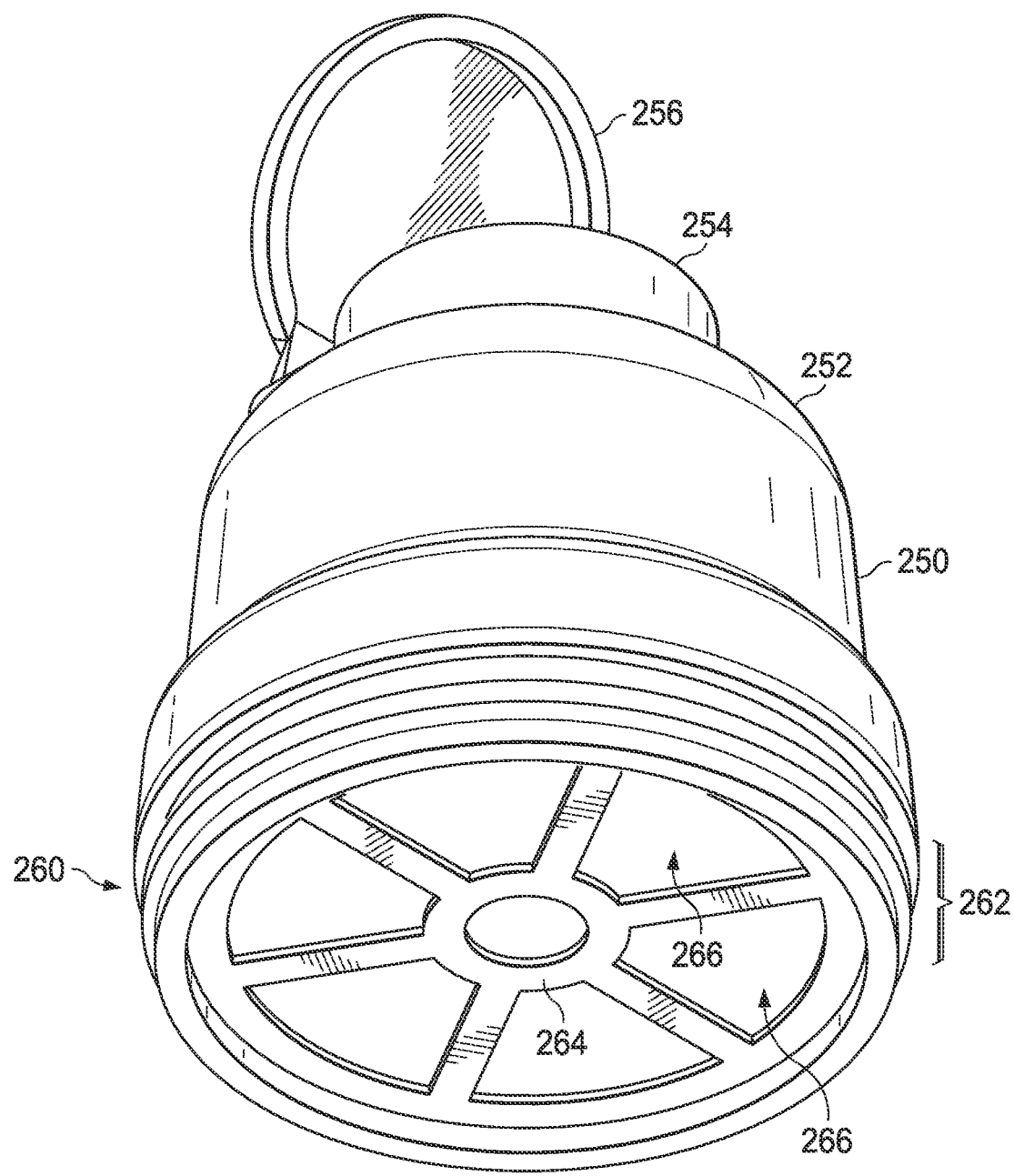

Referring more particularly to FIGS. 4A and B, an alternative illustrated exemplary embodiment of the lid 250 can be either friction fit to the upper end of the container 210 by engaging an upper lip of the container, or can be screwed onto the container 210 by threading 260 on the lower end 262 of lid 250 that engages corresponding threading on the container upper lip (not shown). The lid 250 has a top 252 that has a nozzle 254, equipped with a nozzle closing tab 256, extending from it. Referring briefly to FIG. 2A, when in use, the exemplary container 210 is partially filled with water 272, and a solid 275 or a gel pack 275 that releases the gaseous cleaning agent when in contact with water, is placed in the water container. The cleaning gas begins to evolve more quickly when the motor is activated; gas evolution accelerates due to agitation from rotating impeller 230, as shown by arrow 235, which causes the water to form a vortex in the container 210, as shown. (In some instances it is desirable to allow the solid or gel pack to dissolve at least partially, if not completely, before the motor is activated.) Once sufficient gaseous agent has evolved, the gaseous cleaning agent erupts upward out through the nozzle as an air-borne spray to fill the cabin space and commence cleaning surfaces. Thus, the nozzle 254 has an inner diameter 255 shown in FIG. 4A that is sized to cause gaseous cleaning agent emissions from the container through the nozzle at a speed such that the emissions have both velocity and momentum to cause an air-borne spray that travels throughout the desired region of the cabin space to be cleaned. For example, the air-borne spray velocity is sufficient to travel through the cabin of a car. In other embodiments, such as for a large SUV or a cabin of a tractor trailer rig, more than one apparatus may be needed to achieve total cabin permeation by the air-borne spray. To avoid emitting foam and/or large droplets from the container, the lid includes a baffle 264, exemplified by a cart-wheel structure with spaces between the spokes covered with a fine mesh material 266, in its base area. In addition, the nozzle may include a further baffle 258, at its base, that includes perforations for flow of the gaseous cleaning agent.

While the gaseous cleaning agent has been described as chlorine dioxide, other gaseous agents that perform the same or similar function may also be useful and are encompassed in the claims here below. In addition, odorizing substances may be added to impart a pleasant smell to the interior of the cleaned cabin, or to mask any "chemical" smell.

Figure 5:
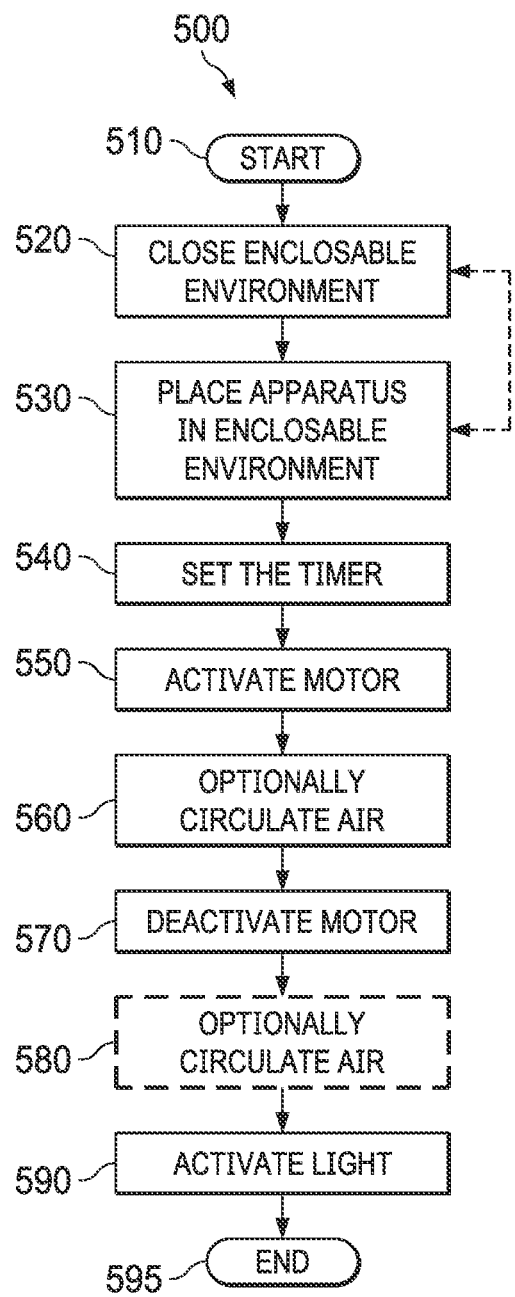
FIG. 5 is a schematic flow diagram of an exemplary embodiment illustrating some of the steps of the method of cleaning contaminated surfaces using a timer-equipped embodiment of an apparatus according to the invention in an enclosed space

Referring to FIG. 5, an exemplary process flowchart, there are several straightforward steps in the system or method 500 depicted that uses a timer-equipped apparatus. Once the process starts at block 510, the enclosable environment with contaminated surfaces inside to be treated is closed at block 520. For example, all doors, windows and the air circulation system, are closed off so that the enclosable environment is essentially closed off from the outside environment. Thus, air does not enter or leave the enclosable environment except for any natural flow around seals of doors and windows, which may occur. Before or after this step, a door is opened, and a timer-equipped apparatus containing liquid with a chemical in solid or gel pack form is placed in the enclosable environment at block 530. (Note that step 520 may take place after step 530; the order is not important, as long as the enclosable environment is closed before the apparatus is activated.). The timer of the apparatus is set in block 540. The timer has a delay to allow an operator to exit the enclosable environment before the motor is activated. This delay can be set to a suitable time, such as 1 or minute, or more, or less, as necessary in the circumstances. After the timer activates the motor of the apparatus in step 550, generating a vortex in the container, the chemical in the apparatus generates a gaseous cleaning agent. An air-borne spray of gaseous cleaning agent and liquid exits upward, as lava from a volcano, and flows throughout the cabin interior, as shown in FIG. 2B by arrows 205. It is theorized, without being bound, that smaller fine liquid droplets are entrained and contact and assist in the coating and permeation of surfaces with the gaseous cleaning agent. The timer allows sufficient time for the cleaning agent to dwell on surfaces and clean these surfaces. Optionally, during this period the air circulation system may be shutdown or may be in recirculation mode as in block 560. If it is in recirculation mode, this would allow the cleaning agent to enter the ducting and filters that form part of the air circulation system and clean these of potential allergens, microbes, viruses and fungi, as well. After the timer expires, the motor is stopped in block 570.

After the motor is stopped, again optionally, the air circulation may be turned on to assist in dissipating the gaseous cleaning agent, as in block 580. After a period of time has elapsed, the expiration light will activate in block 590 signaling to the operator that it is safe to enter the enclosable environment because the gaseous cleaning agent has sufficiently dissipated. The period of elapsed time from motor deactivation to light activation can be set at a suitable time based on whether there is air circulation ongoing or not, and other factors that promote gaseous cleaning agent dissipation. Typically, in the range of about 3 to about 5 minutes. Then in block 595 the cleaning process is completed, and the operator can enter to retrieve the apparatus.

Figure 3A:
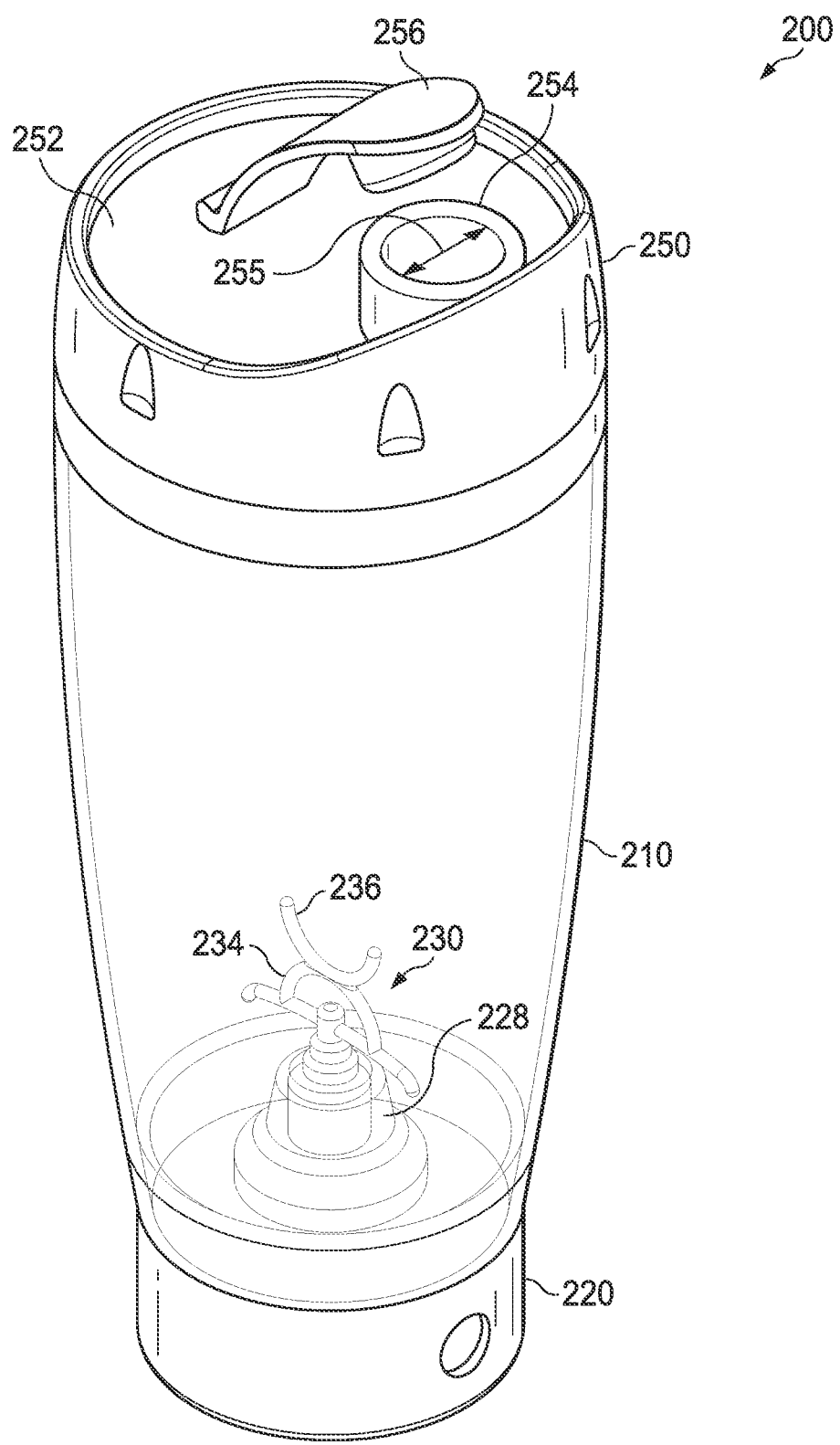
FIG. 3A is a schematic illustration of an exemplary embodiment of an apparatus useful in the methods and systems for cleaning contaminated surfaces in an enclosed space.
Figure 3B:
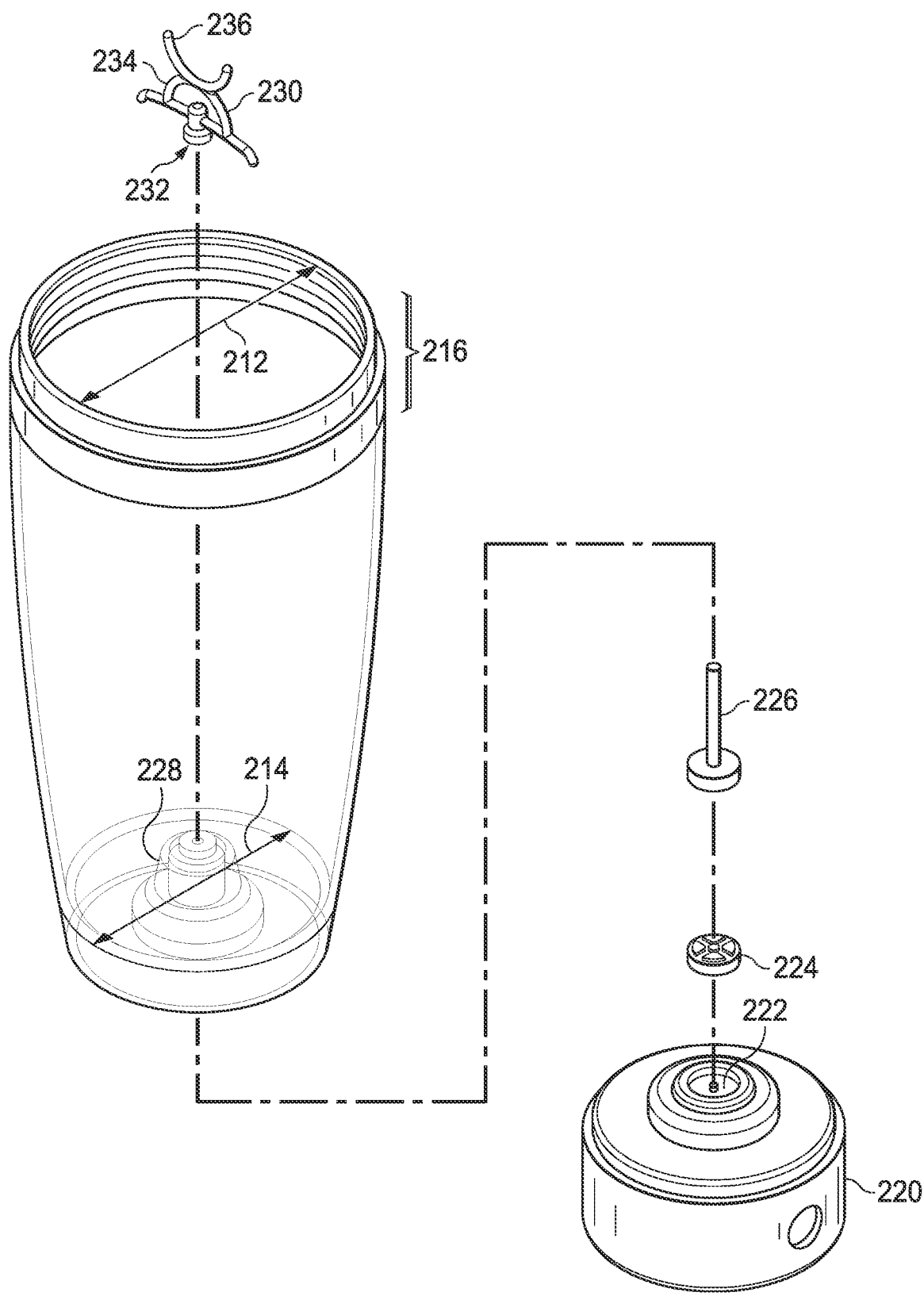
FIG. 3B is an exploded view showing components of the apparatus of FIG. 3A.
Figure 6A:
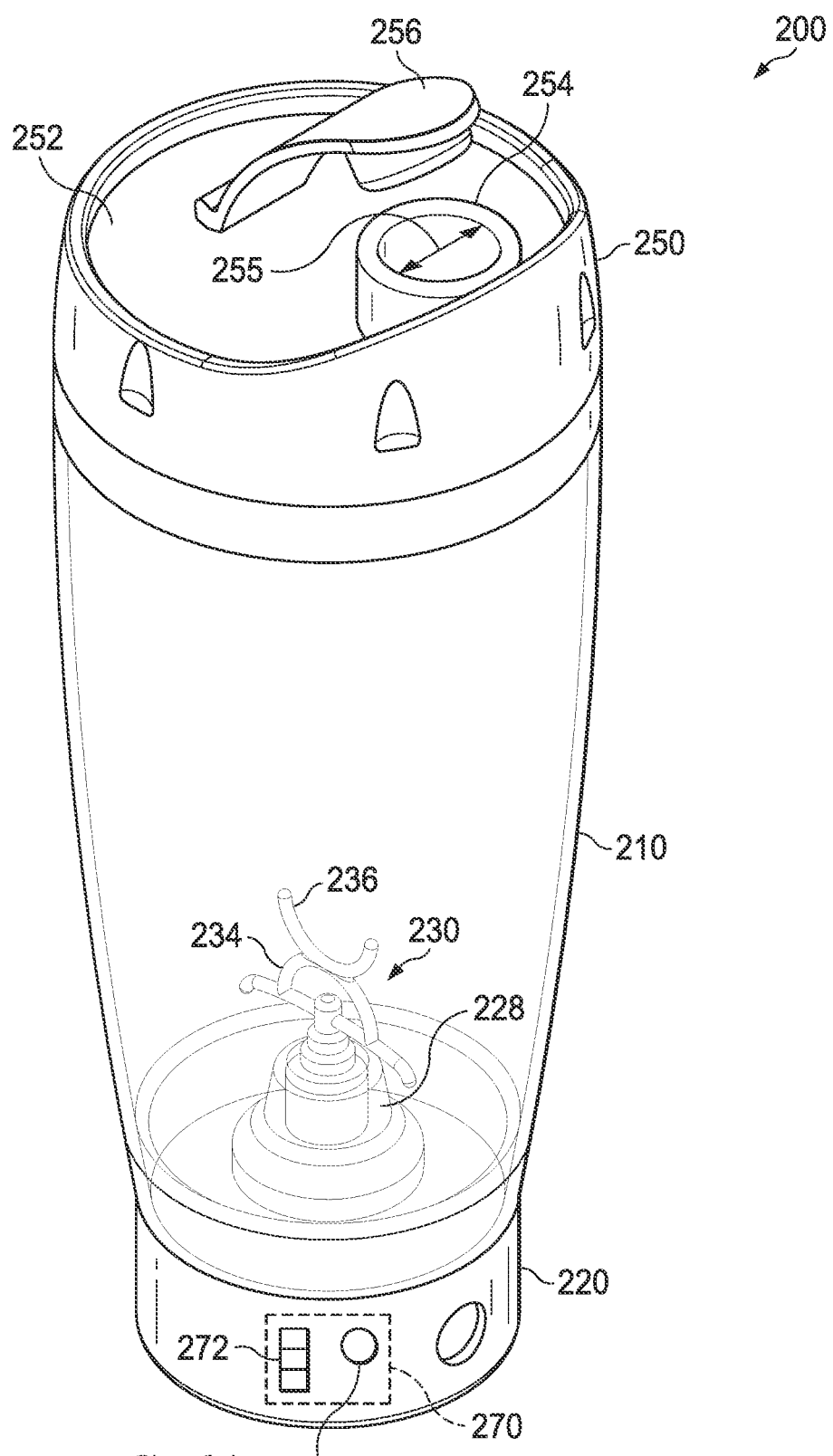
FIG. 6A is an illustrative depiction of an exemplary embodiment of an apparatus according to the invention, equipped with a timer, that is battery-powered with the battery inside the apparatus.
Figure 6B:
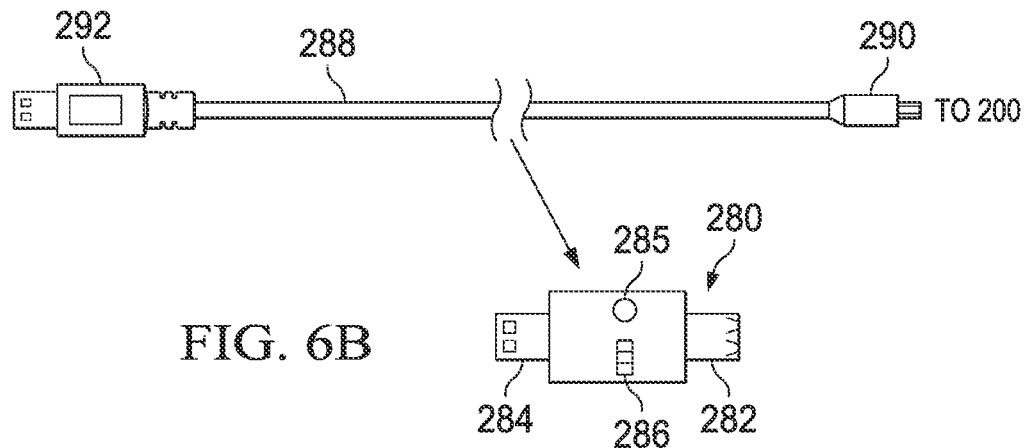
FIG. 6B is an illustrative depiction of an exemplary embodiment of an inline timer for use with an apparatus according to the invention that is corded to receive power and is powered by a power source outside the apparatus.

Referring now to FIG. 6A, depicting an exemplary variant of the embodiment shown in FIG. 3A, the apparatus 200 has a battery housed in the apparatus (not shown), and is equipped with a circuit board 270 having an integrated chip thereon with timer functionality. The circuit board is concealed in the base of the battery-powered apparatus, as shown, but an LED light 272 and a start button 274 both protrude from the base and are easily seen and accessed by an operator. Thus, the timer can be preset for (1) a first time that is a time delay to allow an operator time to leave after the start button 274 is depressed and (2) a second, operating time, that commences after the first time has elapsed, and when the motor (not shown) is activated. Upon elapse of the operating time, the motor is deactivated.

As an exemplary alternative, when the apparatus 200 is not battery powered, but relies on an external power source, the power can be provided, for example, by an electrical cable 288 with connector at one end 292 extending to the power source 292 and connector 290 at the other end plugging into the apparatus 200. The timer may conveniently be carried in a USB-type device 280 with integrated chip (with timer functionality) that can be connected inline in the cable 288, as shown, via opposed ends 282, 284. The USB-type IC timer device has both a start button 285 as well as an indicator light. Of course, other means may also be used, and are within the scope of this disclosure.

Further, the indicator light may be separate from the apparatus 200. Indeed, it may be independently timed. It may also be set apart from the apparatus, for example on the roof of a car being treated, or in the hallway of a hotel outside the room being treated, and the like for convenience.

Figure 7:
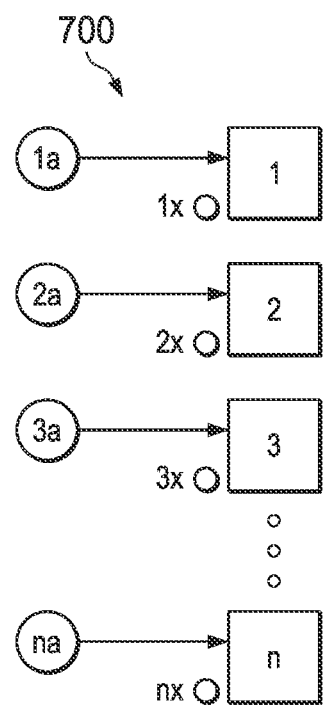
FIG. 7 is an illustrative depiction of the use of a plurality of apparatus according to the invention to treat a plurality of enclosable spaces wherein there are surfaces that may be contaminated.

FIG. 7 depicts schematically in 700 a plurality of enclosable environments (1, 2, 3 . . . n), where n is as many enclosable environments as a lined up in the series comprising the plurality) that are each being serviced by an embodiment of an apparatus (1a, 2a, 3a . . . na) where n is as many apparatus as the enclosable environments) according to the invention. This use of a plurality n of apparatus to treat a plurality n of enclosable environments almost simultaneously, one after the other in rapid succession saves time and is an efficient use of labor. For example, in treating a number of used vehicles, these can be lined up and an operator can place an apparatus in each one after the other. Once he/she reaches the last of the plurality of vehicles n, the indicator light on the first 1x might have lighted up and the apparatus 1a in the vehicle can be retrieved. And so can all the others in series as the indicator lights (1x, 2x, 3x . . . nx) are activated. At the same time cars can be moved and others parked to take their place so that the operation becomes almost continuous.

Of course, in the example of FIG. 7, the enclosable spaces could be hotel rooms along a hallway, compartments on a train, and indeed, any enclosable environments susceptible to more efficient cleaning in series in the manner herein described.

While examples of embodiments of the technology have been presented and described in text and some examples also by way of illustration, it will be appreciated that various changes and modifications may be made in the described technology without departing from the scope of the inventions, which are set forth in and only limited by the scope of the appended patent claims, as properly interpreted and construed.

The invention claimed is:

1. A method of removing malodor from a cabin space comprising the steps of:
   placing water and a formulation comprising a solid or gel pack into a container of an apparatus;
   closing the container with a lid having a nozzle therein;
   sealing the cabin space with the closed container there inside;
   agitating the water and the solid or gel pack with an impeller within the container causing an accelerated release of a gaseous cleaning agent;
   generating an air-borne spray comprising gaseous cleaning agent and water from the lid, the lid configured for knocking out at least some entrained liquid from the air-borne spray prior to exit from the nozzle into the cabin space; and
   allowing the cabin space to remain sealed for an effective time period to eliminate or substantially reduce the malodor.

2. The method of claim 1, wherein the step of sealing the cabin space comprises closing doors, windows and air vents of an air circulation system of a vehicle cabin.

3. The method of claim 1, wherein the step of agitating the water and the solid or gel pack within the container of the apparatus causes the solid or gel pack to accelerate a release of a gaseous cleaning agent comprising chlorine dioxide.

4. The method of claim 3, wherein the step of allowing the cabin space to remain closed is for an effective time period from about 3 to about 20 minutes.

5. The method of claim 3, further comprising: using a detector to determine a concentration of the gaseous cleaning agent in the air within the cabin space, and unsealing the cabin space when the concentration is at a safe level.

6. The method of claim 1, wherein the step of sealing the cabin space comprises closing doors, windows and exterior air vents of an air circulation system of a vehicle cabin; and further comprises turning on an air circulation system of the vehicle cabin.

7. The method of claim 1, wherein the step of allowing the cabin space to remain closed is for an effective time period from about 3 to about 20 minutes.

8. The method of claim 1, further comprising:
   using a detector to determine a concentration of the gaseous cleaning agent in the air within the cabin space, and
   unsealing the cabin space when the concentration is at a safe level.

9. The method of claim 8, wherein the step of using a detector comprises observing an indicator of the apparatus that indicates a concentration of gaseous cleaning agent is at the safe level.

10. The method of claim 1, wherein the step of agitating is caused by the impeller driven by an electric motor.

11. The method of claim 1, wherein the apparatus is powered by connection to a power outlet located within the cabin space.

12. The method of claim 1, wherein the step of sealing the cabin space includes sealing a room of a residential or commercial building.

13. The method of claim 12, wherein the step of generating an airborne spray comprises generating an air-borne spray comprising gaseous chlorine dioxide.

14. The method of claim 1, further comprising:
   placing the apparatus in a cup holder within the cabin space.

15. A method of removing malodor from an enclosable space, the method comprising the steps of:
   selecting, for placement into the enclosable space, a portable apparatus comprising a container;
   adding, into the container of the apparatus, a predetermined quantity of water and a formulation that releases a gaseous cleaning agent;
   putting a lid on the container, wherein the lid includes a nozzle;
   closing the enclosable space to form a closed space;
   starting an air recirculation system of the closed space;
   causing agitation of the quantity of water and the formulation in the container with an impeller;
   emitting an air-borne spray of gaseous cleaning agent from the nozzle of the lid into the closed space; and
   maintaining the closed space closed while allowing the gaseous cleaning agent to dwell within the closed space for an effective time to reduce the malodor.

16. The method of claim 15, wherein the step of closing the enclosable space includes closing doors, windows and exterior air vents of an air circulation system.

17. The method of claim 15, wherein the step of adding the formulation includes adding a solid chemical or gel pack that releases chlorine dioxide upon contact with water.

18. The method of claim 15, wherein the step of maintaining the closed space closed is for an effective time period of at least 15 minutes.

19. The method of claim 15, further comprising using a detector to determine a concentration of the gaseous cleaning agent in the air within the closed space and opening the closed space when the concentration is at a safe level.

20. The method of claim 19, wherein the step of using the detector comprises observing an indicator of the apparatus that indicates the concentration of the gaseous cleaning agent is at a safe level.

21. The method of claim 15, wherein the apparatus is powered by a rechargeable battery.

22. The method of claim 15, wherein the apparatus is powered by connection to a power outlet located within the enclosable space.

23. The method of claim 15, wherein the step of maintaining the enclosable space closed is for an effective time period from about 3 to about 20 minutes.

24. The method of claim 15, wherein the step of maintaining the closed space closed is for an effective time period for removing malodors from the closed space.

\* \* \* \* \*